US 8,777,947 B2

(12) United States Patent
Zahrly et al.

(10) Patent No.: US 8,777,947 B2
(45) Date of Patent: Jul. 15, 2014

(54) TELESCOPING IM NAIL AND ACTUATING MECHANISM

(75) Inventors: Daniel C. Zahrly, Germantown, TN (US); David L. Evans, Bartlett, TN (US); Sied W. Janna, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 28 days.

(21) Appl. No.: 13/109,478

(22) Filed: May 17, 2011

(65) Prior Publication Data

US 2011/0230883 A1    Sep. 22, 2011

Related U.S. Application Data

(63) Continuation-in-part of application No. PCT/US2011/028764, filed on Mar. 17, 2011.

(60) Provisional application No. 61/315,520, filed on Mar. 19, 2010.

(51) Int. Cl.
*A61B 17/58* (2006.01)

(52) U.S. Cl.
USPC .................................. 606/63; 606/62; 606/64

(58) Field of Classification Search
USPC ...................................................... 606/62–64
See application file for complete search history.

(56) References Cited

U.S. PATENT DOCUMENTS

| 5,127,913 | A | 7/1992 | Thomas |
| 5,423,334 | A | 6/1995 | Jordan |
| 5,626,630 | A | 5/1997 | Markowitz et al. |
| 5,681,313 | A | 10/1997 | Diez |
| 5,704,939 | A * | 1/1998 | Justin .............................. 606/63 |
| 5,720,746 | A | 2/1998 | Soubeiran |

(Continued)

FOREIGN PATENT DOCUMENTS

| DE | 19855254 | 6/2000 |
| EP | 1099415 | 5/2001 |

(Continued)

OTHER PUBLICATIONS

International Search Report and Written Opinion for International Application No. PCT/US2012/032340, mailed Sep. 28, 2012.

(Continued)

*Primary Examiner* — Eduardo C. Robert
*Assistant Examiner* — Julianna N Harvey
(74) *Attorney, Agent, or Firm* — Fish & Richardson P.C.

(57) ABSTRACT

A length-adjustable IM nail system includes a telescoping IM nail with proximal and distal bodies. An inner magnet within the proximal body is connected to a threaded rod which, in turn, is connected to the distal body. The threaded rod passes through a threaded block which is connected to the proximal body. The position of the distal end of the threaded rod is fixed with respect to the distal body, but may rotate freely within this fixed position. An actuator is also disclosed that includes a pair of rotating magnets disposed in an angular relationship with each other and the axis of the IM nail and the patient's limb. Rotation of these outer magnets in the same direction results in rotation of the inner magnet and threaded rod and a telescoping axial movement of the threaded block and proximal body with respect to the distal body.

23 Claims, 8 Drawing Sheets

(56) References Cited

U.S. PATENT DOCUMENTS

| | | | |
|---|---|---|---|
| 5,961,553 | A | 10/1999 | Coty et al. |
| 6,261,247 | B1 | 7/2001 | Ishikawa et al. |
| 6,524,313 | B1 | 2/2003 | Fassier |
| 6,658,300 | B2 | 12/2003 | Govari et al. |
| 6,755,862 | B2 | 6/2004 | Keynan |
| 7,001,346 | B2 | 2/2006 | White |
| 7,135,022 | B2 | 11/2006 | Kosashvili et al. |
| 7,218,232 | B2 | 5/2007 | DiSilvestro et al. |
| 7,333,013 | B2 | 2/2008 | Berger |
| 7,474,223 | B2 | 1/2009 | Nycz et al. |
| 7,666,184 | B2 | 2/2010 | Stauch |
| 7,753,915 | B1 | 7/2010 | Eksler |
| 7,932,825 | B2 | 4/2011 | Berger |
| 7,981,025 | B2 | 7/2011 | Pool |
| 8,034,054 | B2 | 10/2011 | Griggs |
| 8,449,543 | B2 | 5/2013 | Pool |
| 2004/0008123 | A1 | 1/2004 | Carrender et al. |
| 2004/0023623 | A1 | 2/2004 | Stauch |
| 2004/0138663 | A1 | 7/2004 | Kosashvili |
| 2004/0153344 | A1 | 8/2004 | Bui et al. |
| 2005/0012617 | A1 | 1/2005 | DilSilvestro et al. |
| 2005/0131397 | A1 | 6/2005 | Levin |
| 2005/0247319 | A1 | 11/2005 | Berger |
| 2005/0261779 | A1 | 11/2005 | Meyer |
| 2006/0004459 | A1 | 1/2006 | Hazebrouck |
| 2006/0142656 | A1 | 6/2006 | Malackowski et al. |
| 2006/0196277 | A1 | 9/2006 | Allen et al. |
| 2006/0235424 | A1 | 10/2006 | Vitale et al. |
| 2006/0247773 | A1 | 11/2006 | Stamp |
| 2006/0293683 | A1 | 12/2006 | Stauch |
| 2007/0265690 | A1 | 11/2007 | Lichtenstein et al. |
| 2008/0033436 | A1* | 2/2008 | Song et al. ............ 606/61 |
| 2008/0094275 | A1 | 4/2008 | Laroche |
| 2008/0108995 | A1 | 5/2008 | Conway |
| 2008/0119856 | A1 | 5/2008 | Gotfried |
| 2008/0170473 | A1 | 7/2008 | Kaiser et al. |
| 2008/0294258 | A1 | 11/2008 | Revie et al. |
| 2009/0076597 | A1 | 3/2009 | Dahlgren |
| 2009/0112262 | A1 | 4/2009 | Pool |
| 2009/0131838 | A1 | 5/2009 | Fotiadis et al. |
| 2009/0222050 | A1 | 9/2009 | Wolter et al. |
| 2009/0254088 | A1* | 10/2009 | Soubeiran ............ 606/63 |
| 2010/0049204 | A1 | 2/2010 | Soubeiran |
| 2010/0152584 | A1 | 6/2010 | Ariav et al. |
| 2010/0228167 | A1 | 9/2010 | Ilovich |
| 2011/0060336 | A1 | 3/2011 | Pool et al. |
| 2011/0137347 | A1 | 6/2011 | Hunziker |
| 2011/0196435 | A1 | 8/2011 | Forsell |
| 2011/0230883 | A1 | 9/2011 | Zahrly |
| 2011/0238126 | A1 | 9/2011 | Soubeiran |
| 2012/0130428 | A1 | 5/2012 | Hunziker |
| 2012/0179215 | A1 | 7/2012 | Soubeiran |
| 2012/0209269 | A1 | 8/2012 | Pool |
| 2012/0296234 | A1 | 11/2012 | Wilhelm |
| 2013/0072932 | A1 | 3/2013 | Stauch |

FOREIGN PATENT DOCUMENTS

| | | |
|---|---|---|
| EP | 1560533 A1 | 8/2005 |
| EP | 1704893 A1 | 9/2006 |
| EP | 2151208 A2 | 2/2010 |
| EP | 1764050 B1 | 5/2010 |
| EP | 2380514 A1 | 10/2011 |
| EP | 2173267 B1 | 11/2011 |
| WO | WO9626678 | 9/1996 |
| WO | WO9714367 | 4/1997 |
| WO | WO9720512 | 6/1997 |
| WO | WO0032124 | 6/2000 |
| WO | WO0124697 | 4/2001 |
| WO | WO2004045431 A1 | 6/2004 |
| WO | WO2006113660 | 10/2006 |
| WO | WO2007061890 | 5/2007 |
| WO | WO2008015679 | 2/2008 |
| WO | WO2013126027 A1 | 8/2013 |

OTHER PUBLICATIONS

Mendes, et al., "IntelliJoint System for monitoring displacement in biologic system", Biomed Bytes 2002 (4), pp. 69-70.

Global market for RFID in healthcare 2006-2016 by value: Source: IDTechEx, RFID in Healthcare 2006-2016, May 1, 2006.

Clyde Church, "Radio Frequency Identification (RFID) Tracking of Orthopaedic Inventories Fact or Fiction, Today and Tomorrow," BONE Zone, Spring 2004, pp. 35-40.

International Search Report and Written Opinion for International Application No. PCT/US2011/028764, mailed Nov. 23, 2011, 11 pages.

International Preliminary Report on Patentability for International Application No. PCT/US2012/038248, mailed Nov. 28, 2013.

International Preliminary Report on Patentability for International Application No. PCT/US2012/032340, mailed Nov. 19, 2013.

* cited by examiner

TELESCOPING IM NAIL AND ACTUATING MECHANISM

BACKGROUND

1. Technical Field

This disclosure relates to a limb lengthening intramedullary (IM) nail that includes a telescoping structure and a magnetic actuating mechanism. More specifically, an IM nail is disclosed that includes a telescoping structure with an internal magnet and an external actuating mechanism that includes rotating magnets for non-invasive lengthening (distraction) or shortening (contraction) of the IM nail as needed.

2. Description of the Related Art

A variety of treatments for limb length discrepancies are known. Limb length discrepancies may arise from birth defects, improper bone growth, disease, or trauma. Treatments of leg length discrepancies include the use of shoe lifts and special boots to raise the foot in the equinus position. The field of orthopedics includes other techniques, such as stimulating epiphyseal growth, surgical shortening of the longer limb, and surgical lengthening of the short limb. Current limb lengthening techniques generally apply Ilizarov's principle of tension-stress, wherein living tissue subjected to slow, steady tension becomes metabolically activated. Hence, upon the creation of a bone gap and a subsequent distraction of the gap, new bone may be formed to generate an increase in length. In current limb lengthening techniques, bone of the limb is cut, called an osteotomy or corticotomy. The bone begins development of a callus at this location. The two bone portions are then pulled apart by a mechanical device that is surgically attached to the bone. This procedure is called distraction, in which the callus is stretched, thereby lengthening the bone.

The current mechanical devices used for limb lengthening include external fixators in the form of rings, connected by adjustable struts and that are transcutaneously connected to the bone using wires, pins, or screws.

Various length-adjustable IM nails include: shape memory alloys to lengthen a telescopic IM nail; implanted electric motors to provide a distraction force; hydraulic or pneumatic mechanisms or pumps; ratchet mechanisms; magnetically driven gear mechanisms; and some designs exploit movement by the patient to generate the distraction force.

SUMMARY OF THE DISCLOSURE

A length-adjustable IM nail and an actuator for distracting or contracting the disclosed IM nail are disclosed.

One disclosed IM nail comprises a proximal outer body that includes a proximal end and a distal end. The distal end of the outer body receives a portion of a distal body. The proximal outer body also accommodates an inner magnet. The inner magnet is coupled to a proximal end of a threaded shaft. The threaded shaft also includes a distal end that is rotatably coupled to the distal body. Further, the threaded shaft passes through a threaded block that is coupled to the proximal outer body.

As a result, rotation of the inner magnet and threaded shaft causes axial movement of the proximal outer body with respect to the distal body. In one embodiment, the distal end of the threaded shaft, while rotatably connected to the distal body, is connected to the distal body at a fixed position. That is, the shaft can rotate at the fixed position, but does not move with respect to the distal body.

An actuator is also disclosed that includes at least one outer magnet. The outer magnet is rotatably accommodated in its own housing, equipped with a drive mechanism for rotating the outer magnet about an axis that is parallel to the axis of the inner magnet of an IM nail. Imparting rotation to the outer magnet imparts rotation to the inner magnet disposed within the proximal outer body of the IM nail. Rotation of the inner magnet results in rotation of the threaded shaft, which imparts axial movement of the threaded block. The axial movement of the threaded block causes axial movement of the proximal outer body with respect to the distal body.

An actuator is also disclosed for increasing the torque applied to the inner magnet. Instead of a single magnet, the actuator includes first and second outer magnets. Each outer magnet is rotatably accommodated in its own housing and at an axis that is parallel to the axis of the inner magnet and IM nail. The housing of the first and second outer magnets are coupled together to maintain the first and second outer magnets in a spaced-apart angular relationship that permits the IM nail (and the patient's limb) to be positioned between the first and second outer magnets. A linkage couples the first and second outer magnets together and is capable of imparting rotation to the first and second outer magnets in the same direction which imparts rotation to the inner magnet and threaded shaft.

In a refinement, an angle defined by the inner magnet (as the apex) and the first and second outer magnets can range from about 120 to about 180°. Angles of less than 120° may result in the two outer magnets generating some opposing forces instead of cooperating forces.

In a refinement, the distal body comprises an elongated slot. The threaded block comprises a radial extension that extends through the slot of the distal body and that is coupled to the proximal outer body for causing axial movement of the proximal outer body with respect to the distal body when the threaded block moves axially as a result of rotation of the threaded shaft.

In another refinement, the distal end of the threaded shaft is rotatably received in a distal block that is coupled to the distal body for coupling the distal end of the threaded shaft to the distal body. In a further refinement of this concept, the threaded shaft passes through the distal block and is coupled to an end cap. The threaded shaft is free to rotate within the distal block but the end cap serves to maintain the position of the distal end of the threaded shaft in a fixed position within the distal body because at least one of the distal block or the end cap is fixed to the distal body.

In other refinement, the first outer magnet is coupled to a drive mechanism. Further, the linkage that couples the first and second outer magnets together translates rotation imparted to the first outer magnet by the drive mechanism to rotation of the second outer magnet. In a further refinement of this concept, the linkage is a linkage assembly that comprises a first linkage that couples the first outer magnet to an arcuate linkage that couples the first linkage to a second linkage that couples the arcuate linkage to the second outer magnet. In still a further refinement of this concept, the drive mechanism is activated by a switch disposed on the housing of the first outer magnet.

In other refinement, the first and second outer magnets rotate about parallel axes and in the same direction to increase the torque imposed on the inner magnet disposed within the outer body of the IM nail.

In another refinement, the arcuate linkage is accommodated in an arcuate housing that couples the housings of the first and second outer magnets together to maintain the first and second outer magnets in an angular relationship of about 120 to about 180° with respect to each other, with the axis of the inner magnet being the apex and the rotational axes of all three magnets being parallel or as close to parallel as feasible, given the operation conditions.

In a refinement, the distal body of the IM nail includes at least one transverse hole for receiving a fixation element to couple the distal body to a patient's bone.

In another refinement, the actuator comprises a user interface that displays the magnitude of the axial distraction or axial compaction of the IM nail.

In a refinement, the inner magnet is disposed within a carrier or casing that is coupled to the proximal end of a threaded shaft.

One, two and three magnet actuators are disclosed.

A method for adjusting the length of an IM nail is also disclosed which includes providing an IM nail as disclosed above, providing an actuator as disclosed above and placing the actuator so an outer magnet is disposed relative to the IM nail, and rotating the outer magnet to impart rotation to the inner magnet and threaded shaft which imparts axial movement of the threaded block and proximal outer body with respect to the distal body.

A rotation axis of the outer magnet may be parallel to, perpendicular to, or non-parallel to an axis of the intramedullary nail.

According to some aspects of the present invention there may be provided a length adjustable intramedullary nail system, including: an intramedullary (IM) nail comprising a proximal outer body comprising a proximal end and a distal end, the distal end of the proximal outer body receiving a portion of a distal body, the proximal outer body accommodating an inner magnet, the inner magnet being coupled to a proximal end of a threaded shaft, the threaded shaft comprising a distal end rotatably coupled to the distal body, the threaded shaft passing through a threaded block, the threaded block being coupled to the proximal outer body; and an actuator comprising at least one outer magnet rotatably accommodated in its own housing, the housing of the outer magnet rotatably holding the outer magnet along an axis that is substantially parallel to an axis of the inner magnet, the actuator further comprising a drive mechanism that imparts rotation to the inner magnet and threaded shaft which imparts axial movement of the threaded block and proximal outer body with respect to the distal body.

According to some embodiments, the distal body has an elongated slot, the threaded block has a radial extension that extends through the slot and that is coupled to the proximal outer body.

According to some embodiments, the distal end of the threaded shaft is rotatably received in a distal block that is coupled to the distal body for coupling the distal end of the threaded shaft to the distal body.

According to some embodiments, the distal end of the threaded shaft passes through a distal block and is coupled to an end cap, the threaded shaft is free to rotate within the distal block, at least one of the distal block or end cap fixing the threaded shaft to the distal body.

According to some embodiments, the actuator further comprises a first outer magnet is coupled to a drive mechanism and a linkage that couples the first outer magnet to a second outer magnet wherein rotation imparted to the first outer magnet by the drive mechanism also results in rotation to the second outer magnet.

According to some embodiments, the linkage is a linkage assembly that comprises a first linkage that couples the first outer magnet to an arcuate linkage that couples the first linkage to a second linkage that couples the arcuate linkage to the second outer magnet.

According to some embodiments, the drive mechanism is activated by a switch disposed on the housing of the first outer magnet.

According to some embodiments, the first and second outer magnets rotate about parallel axes and in a same direction.

According to some embodiments, the arcuate linkage is accommodated in an arcuate housing that couples the housings of the first and second outer magnets together to maintain the first and second outer magnets in angular relationship with respect to each other, wherein an angle defined by an axis of the first outer magnet, an axis of the inner magnet and an axis of the second outer magnet, with the axis of the first outer magnet as the apex, ranges from about 120 to about 180°.

According to some embodiments, the distal body of the IM nail includes at least one transverse hole for receiving a fixation element to couple the distal body to bone.

According to some embodiments, the actuator comprises a user interface that displays an axial distraction or an axial compaction of the IM nail.

According to some aspects, an actuator includes at least one magnet having an axis oriented to be non-parallel to an axis of an intramedullary nail, and the magnet is configured for rotation about the magnet axis. A user interface displays the magnitude of axial distraction or axial compaction of an intramedullary nail caused by rotation of the magnet.

According to some embodiments, the actuator includes at least a second magnet coupled to the first magnet and having an axis oriented to be non-parallel to the intramedullary nail axis. The second magnet is configured for rotation about the second magnet axis. Alternatively, the second magnet has an axis oriented parallel to the intramedullary nail axis.

According to some aspects of the present invention there may be provided length-adjustable intramedullary (IM) nail, including: a proximal outer body comprising a proximal end and a distal end; the distal end of the proximal outer body receiving a portion of a distal body; the proximal outer body accommodating an inner magnet, the inner magnet being coupled a proximal end of a threaded shaft; the threaded shaft comprising a distal end rotatably coupled to the distal body at a fixed position, the threaded shaft passing through a threaded block, the threaded block being coupled to the proximal outer body; and wherein rotation of the inner magnet imparts rotation to the threaded shaft which imparts axial movement of the threaded block and proximal outer body with respect to the distal body.

According to some embodiments, the distal body includes an elongated slot, the threaded block includes a radial extension that extends through the slot and that is coupled to the proximal outer body.

According to some embodiments, the distal end of the threaded shaft is rotatably received in a distal block that is coupled to the distal body for coupling the distal end of the threaded shaft to the distal body.

According to some embodiments, the distal end of the threaded shaft passes through a distal block and is coupled to an end cap, the threaded shaft is free to rotate within the distal block, at least one of the distal block or end cap fixing the threaded shaft to the distal body.

According to some embodiments, the distal body of the IM nail includes at least one transverse hole for receiving a fixation element to couple the distal body to bone.

According to some aspects of the present invention there may be provided a method of adjusting the length of an intramedullary (IM) nail, the method including: providing an intramedullary (IM) nail comprising a proximal outer body comprising a proximal end and a distal end, the distal end of the proximal outer body receiving a portion of a distal body, the proximal outer body accommodating an inner magnet, the inner magnet being coupled a proximal end of a threaded shaft, the threaded shaft comprising a distal end rotatably coupled to the distal body, the threaded shaft passing through a threaded block, the threaded block being coupled to the proximal outer body; placing an actuator comprising first and second outer magnets around the IM nail so the first and second outer magnets are disposed on either side of the inner magnet; and rotating the first and second outer magnets to impart rotation to the inner magnet and threaded shaft which imparts axial movement of the threaded block and proximal outer body with respect to the distal body.

According to some embodiments, the distal body includes an elongated slot, the threaded block comprising a radial extension that extends through the slot and that is coupled to the proximal outer body, axial movement of the proximal outer body with respect to the distal body results in movement of the radial extension along the slot.

According to some embodiments, the method further includes the step of fixing the distal end of the threaded shaft to the distal body so the threaded shaft may rotate within the distal body but has a fixed axial position with respect to the distal body.

According to some embodiments, the method further includes the step of coupling the first outer magnet to a drive mechanism and a linkage assembly that couples the first and second outer magnets together wherein rotation imparted to the first outer magnet by the drive mechanism also imparts rotation to the second outer magnet.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiments illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

Figure 1:
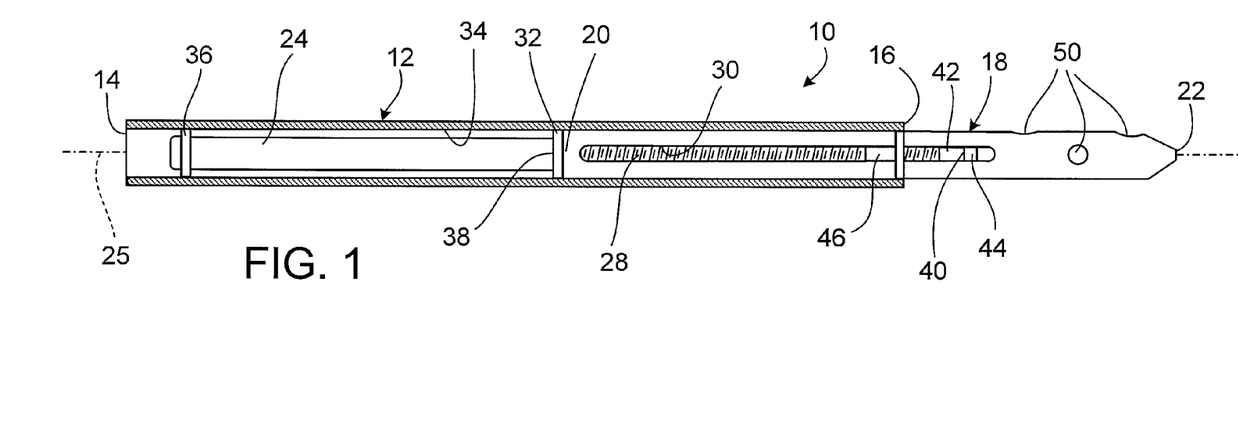
FIG. 1 is a plan view of an IM nail made in accordance with this disclosure.

FIG. 1 is a plan view of a disclosed telescoping IM nail 10. The IM nail 10 includes a proximal outer body 12 having a proximal end 14 and a distal end 16. The distal end 16 of the proximal outer body 12 accommodates at least a portion of a distal body 18. The distal body 18 also includes a proximal end 20 and a distal end 22. The proximal outer body 12, in addition to accommodating at least a portion of the distal body 18, also accommodates an inner magnet 24. The inner magnet 24 may be accommodated in a casing or carrier to facilitate the coupling of the inner magnet 24 to the threaded rod 28. The inner magnet 24 may be rotated about the axis 25 of the IM nail 10 by the actuator 26 illustrated in FIGS. 3-6 and discussed below.

Returning to FIG. 1, the inner magnet 24 is coupled to a threaded rod 28 which can be seen extending through the elongated slot 30 of the distal body 18. The threaded rod 28 passes through the proximal end 20 of the distal body 18 and a bearing 32 before being coupled to the inner magnet 24. The bearing 32 engages the inner wall 34 of the proximal outer body 12. Similarly, a proximal bearing 36 is coupled to the inner magnet 24 to facilitate rotation of the inner magnet 24 within the proximal outer body 12.

The threaded rod 28 includes a proximal end 38 coupled to the inner magnet 24 and a distal end 40 that is accommodated within a distal block 42 and connected to an end cap 44. The threaded rod 28 also passes through a threaded block 46. The threaded block 46 is coupled to the proximal outer body 12. Hence, rotation of the inner magnet 24 (or carrier) results in rotation of the threaded rod 28 and rotation of the threaded rod 28 within the threaded block 46. Because the threaded block 46 is coupled to the proximal outer body 12, rotation of the inner magnet 24 and threaded rod 28 results in axial movement of the proximal outer body 12 in either direction along the axis 25 of the IM nail 10. At least one of the distal block 42 or end cap 44 is fixed to the distal body 18 so the position of the distal end 40 of the threaded rod 28 is fixed in the position shown in both FIGS. 1 and 2 with respect to the distal body 18. The distal body 18 also includes a plurality of openings 50 for coupling the distal body 18 to the patient's bone.

Figure 2:
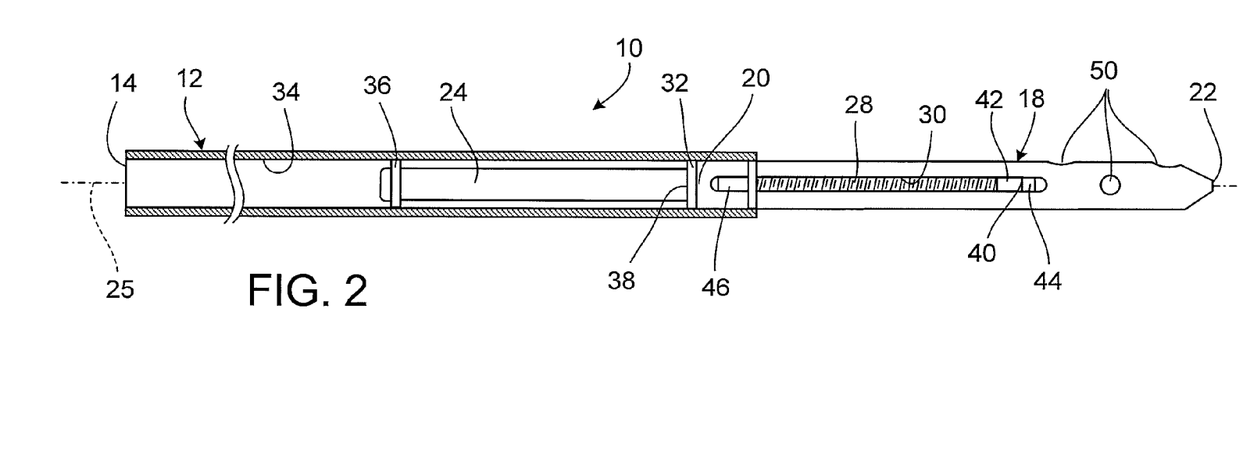
FIG. 2 is a plan view of the IM nail disclosed in FIG. 1 illustrating the IM nail in a distracted or extended position.

Turning to FIG. 2, the inner magnet 24 has been rotated resulting in rotation of the threaded rod 28 and movement of the threaded block 46 and outer body to the left as shown in FIG. 2 which results in a distraction or lengthening of the IM nail 10. The rotation of the inner magnet 24 is caused by the actuator 26 illustrated in FIGS. 4-6. In comparing FIGS. 1 and 2, the reader will note that the positions of the distal block 42, end cap 44 and distal end 40 of the threaded rod 28 with respect to the distal body 18 remain unchanged. The elongated slot 30 disposed within the distal body 18 provides for a convenient means for sliding the threaded block 46 in either direction along the axis 25 of the IM nail 10.

Figure 3:
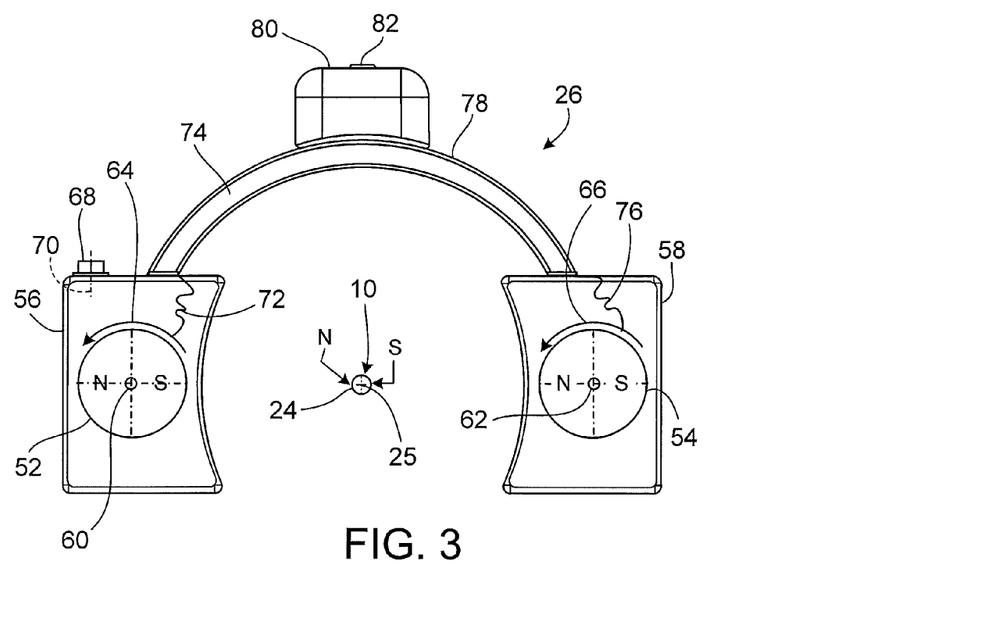
FIG. 3 is an end view of a disclosed actuator mechanism in position and surrounding a disclosed IM nail (the patient's limb is not shown)

Turning to FIG. 3, one disclosed actuator 26 is shown in a position where it surrounds the IM nail 10. The inner magnet is shown at 24 and the north-south coordinates for the inner magnet 24 as well as the first and second magnets 52, 54 are also illustrated. The first and second outer magnets 52, 54 are each accommodated within housings 56, 58. The first and second magnets 52, 54 are rotatable about axes 60, 62 that are generally parallel with the axis 25 of the IM nail 10. Rotation of the first and second outer magnets 52, 54 about the axes 60, 62 in the same direction or in the direction of the arrows 64, 66 imparts rotation to the inner magnet 24 and threaded rod 28 (FIGS. 1-2).

Figure 4:
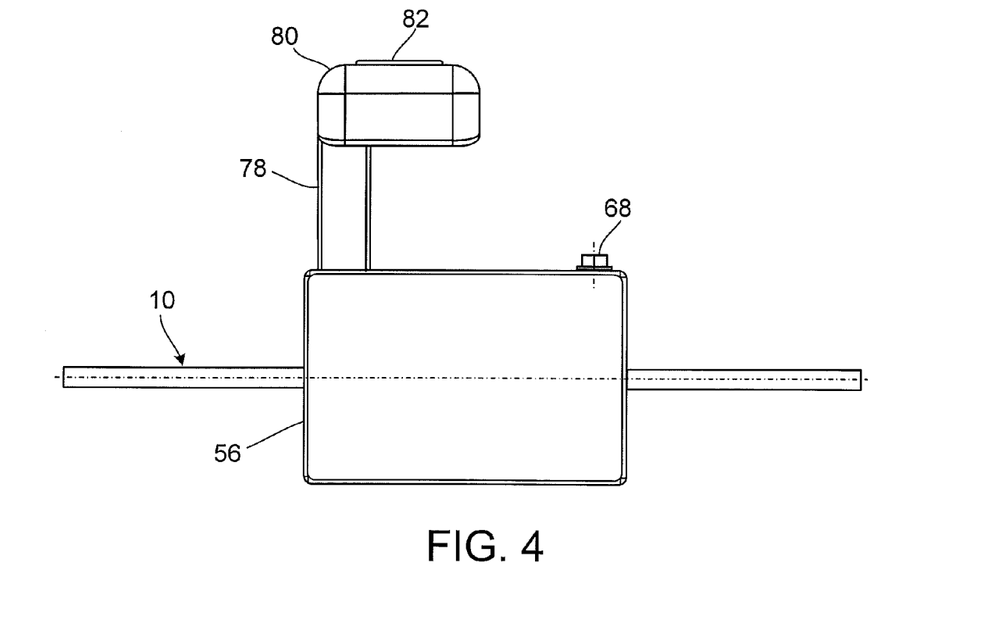
FIG. 4 is a side view of the actuator and IM nail disclosed in FIG. 3.
Figure 5:
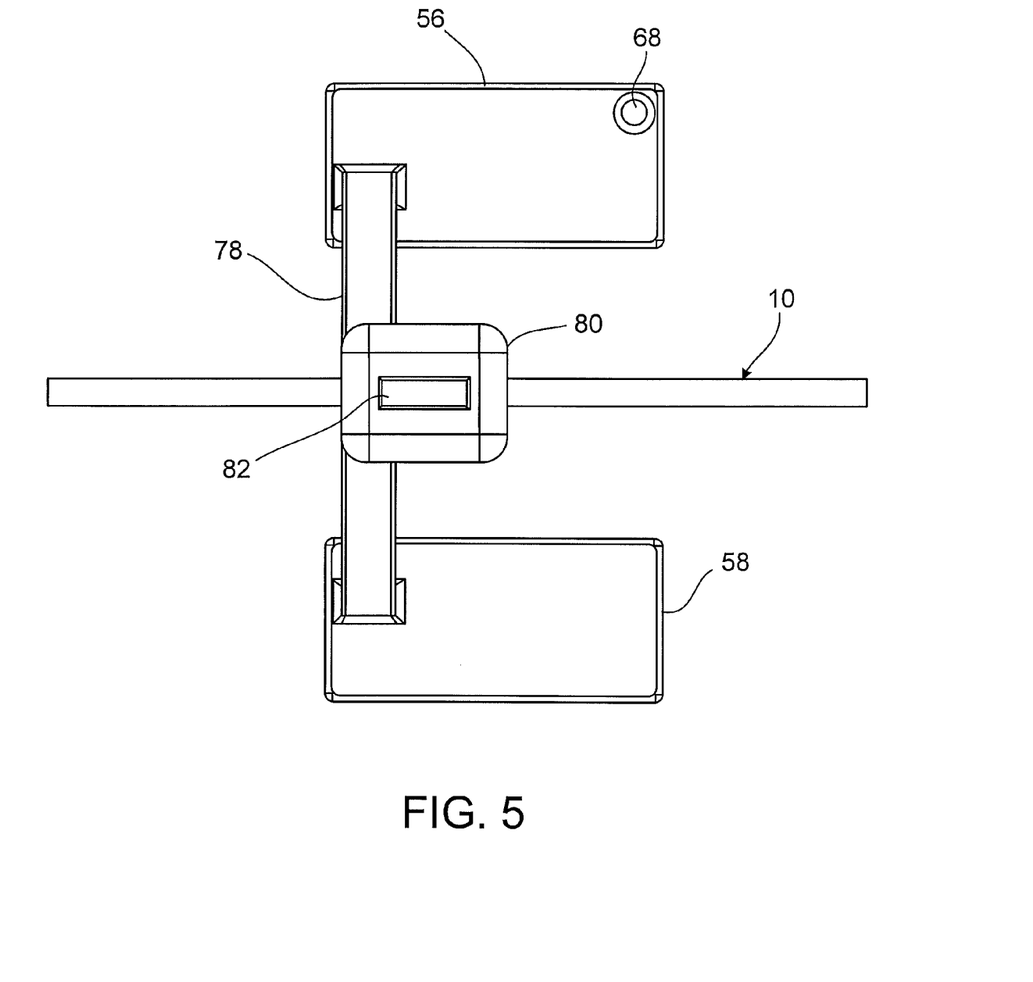
FIG. 5 is a top plan view of the actuator and IM nail disclosed in FIGS. 3-4.
Figure 6:
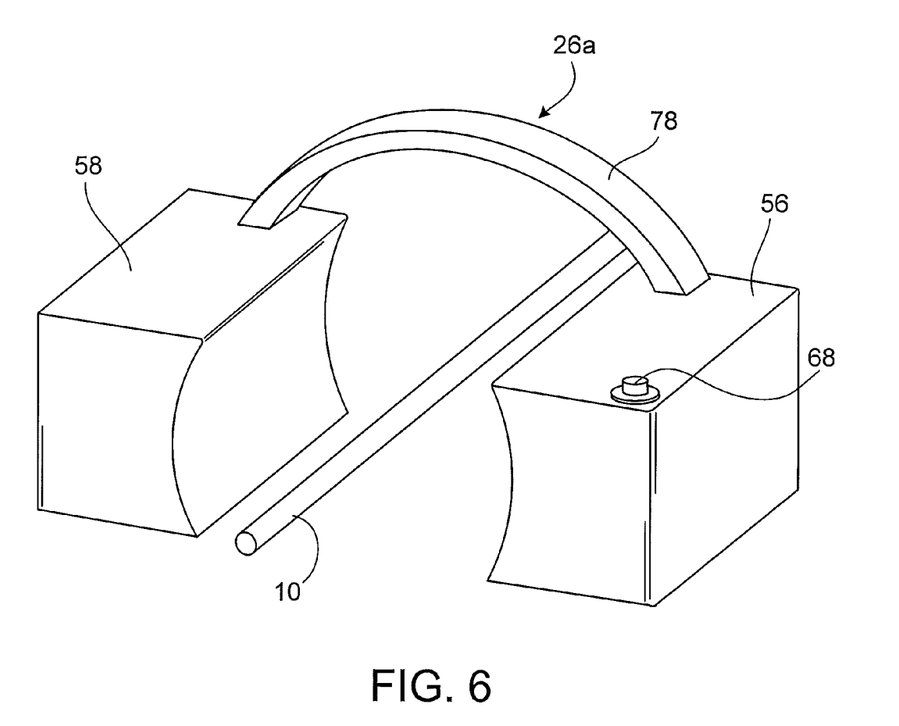
FIG. 6 is a perspective view of a disclosed actuator and IM nail.

Rotation of the first and second outer magnets 52, 54 may be initiated by an actuator button 68. The actuator button 68 may be used to activate a drive mechanism shown schematically at 70 which rotates the first outer magnet 52 in the direction of the arrow 64. The first outer magnet 52 may be coupled to a linkage 72 which, in turn, is coupled to an arcuate linkage 74 which, in turn, is coupled to a linkage 76 which imparts rotation to the second outer magnet 54 in the direction of the arrow 66. The arcuate linkage 74 may be accommodated in an arcuate housing 78 which may also be used to support a user interface 80 for indicating to the surgeon or physician the amount of distraction or compaction imposed on the IM nail 10 as the result of operating the actuator 26. Preferably, the interface 80 is supported on the arcuate housing 78 so that a display panel 82 is readily visible to the physician or surgeon. As illustrated in FIGS. 4 and 5. An additional perspective view of an actuator 26a is illustrated in FIG. 6.

Figure 9:
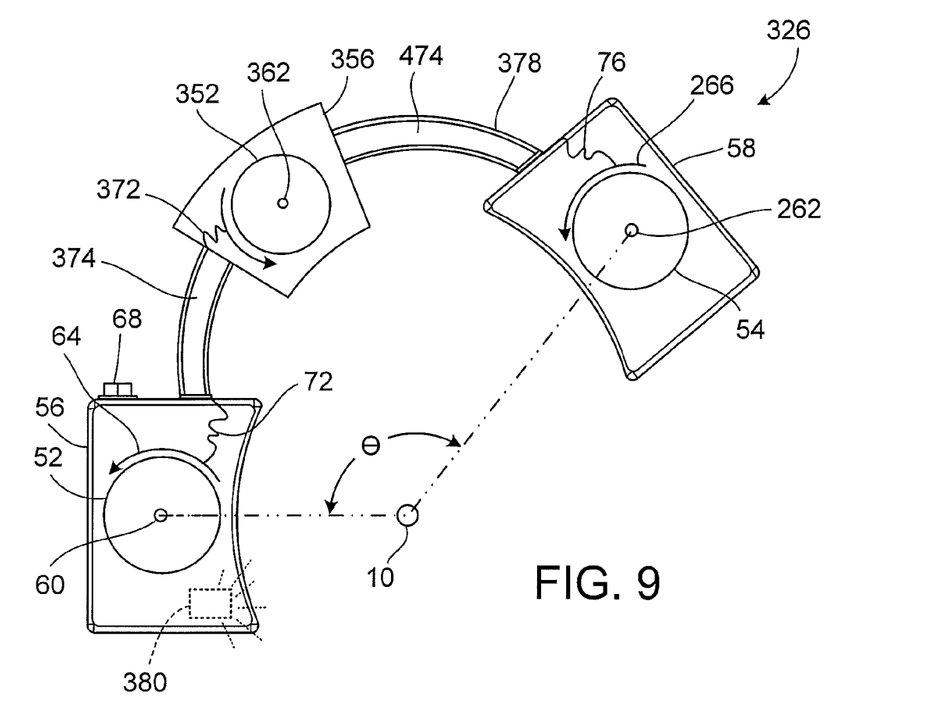
FIG. 9 is an end view of a disclosed three-magnet actuator mechanism in position and surrounding a disclosed IM nail (the patient's limb is not shown)
Figure 10:
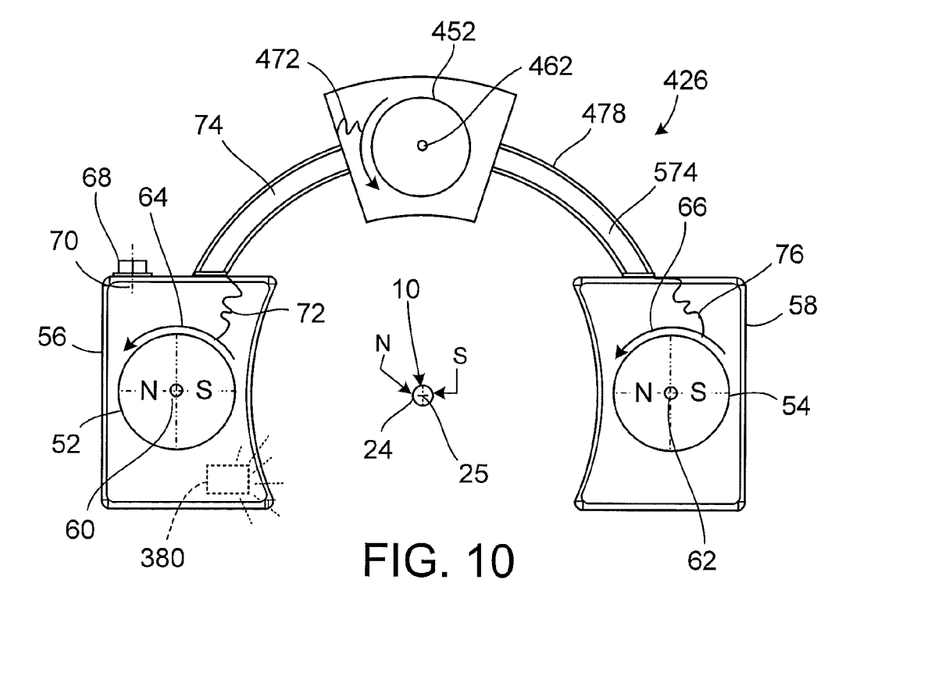
FIG. 10 is an end view of another disclosed three-magnet actuator mechanism in position and surrounding a disclosed IM nail (the patient's limb is not shown)

The linkages 70, 72, 74, 76, 274 (FIG. 8) may include any one or more of a flexible drive mechanism, gearing combinations, belt drives, worm gears, hydraulic drives, pneumatic drives, hydrostatic drives, chain drives, and bar linkage drives. The actuator 68 and linkage 70 may be a motor, such as a stepper motor with a shaft (not shown) coupled to the outer magnet 52. The magnet 52 may also be driven by a motor (not shown) with drive belts, gear, worm gears, chain drive, etc., linking the magnet 52 to the other magnet(s) 54, 352, 452 (FIGS. 9-10). Each magnet may also be equipped with its own motor with the motors controlled by a microprocessor (not shown). In short, one skilled in the art will appreciate that an abundance of options exist for imparting rotational motion to the magnet(s) 52, 54, 352, 452.

Figure 7:
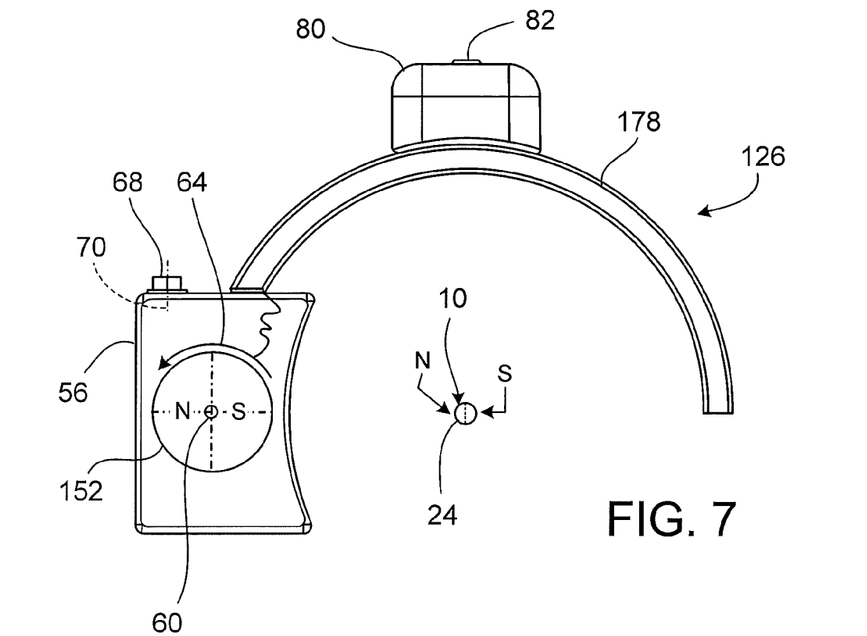
FIG. 7 is an end view of another disclosed single-magnet actuator mechanism in position and surrounding a disclosed IM nail (the patient's limb is not shown)

Turning to FIG. 7, another disclosed actuator 126 is shown with a single outer magnet 152. The arcuate housing 178 surrounds the IM nail 10. The inner magnet is shown at 24 and the north-south coordinates for the inner magnet 24 as well as the single magnet 152 are also illustrated. The outer magnet 152 is accommodated within a housing 56 and is rotatable about the axis 60 that are generally parallel with the axis 25 of the IM nail 10. The actuator 126 of FIG. 6 will generally impose less torque on the inner magnet 24 than the actuator 26 of FIG. 3.

Figure 8:
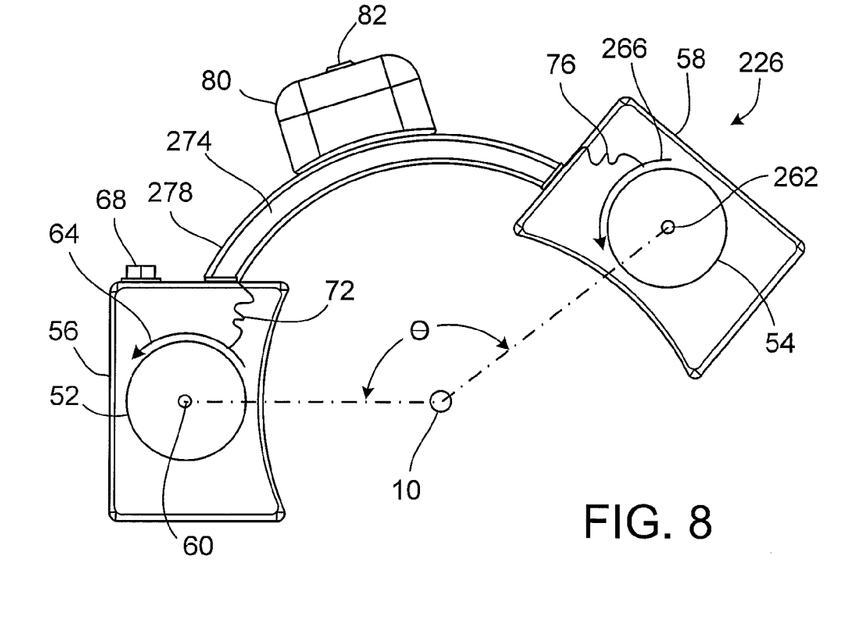
FIG. 8 is an end view of another disclosed two-magnet actuator mechanism in position and surrounding a disclosed IM nail (the patient's limb is not shown)

Turning to FIG. 8, another two-magnet actuator 226 is shown in a position where it surrounds the IM nail 10. The first and second outer magnets 52, 54 are each accommodated within housings 56, 58 but the arcuate housing 278 and linkage 227 has been modified to support the magnets 52, 54 so their respective axes 60, 262 at an angle θ of about 120° with respect to each other, using the nail axis 25 as the apex. Rotation of the first and second outer magnets 52, 54 about the axes 60, 262 in the same direction or in the direction of the arrows 64, 266 imparts rotation to the inner magnet 24 and threaded rod 28 (FIGS. 1-2). The angle θ may range from about 120 to about 180°. Further, the single magnet actuator 126 may also be used, but some operators may choose a magnet 152 (FIG. 7) that is stronger than the magnet 52 (FIGS. 3 and 8).

FIGS. 9 and 10 illustrate three-magnet actuators 326, 426. Middle magnet 352, 452 are disposed between the first and second magnets 52, 54. Additional linkages 372, 472, 474, 574 are shown. The three magnet actuators 326, 426 are ideal for incorporating a wireless communications interface 380 as discussed above.

Figure 11:
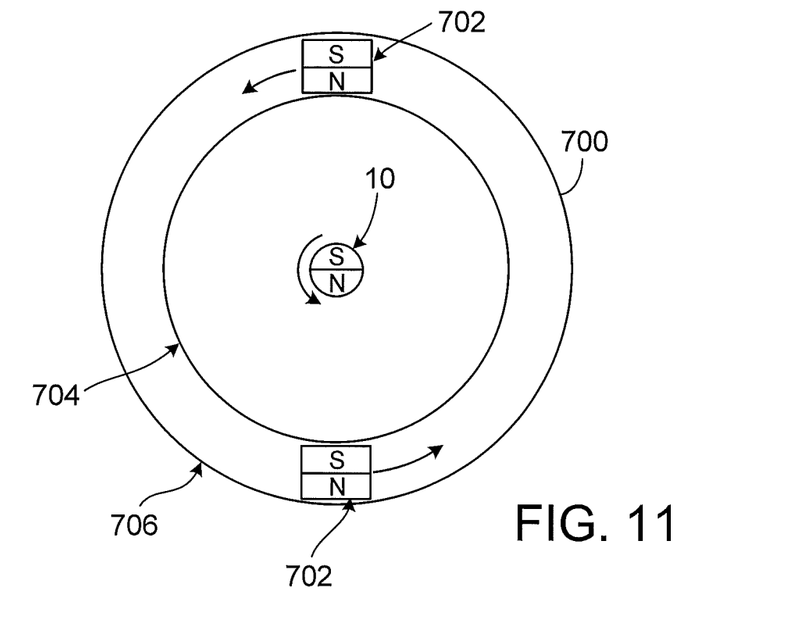
FIG. 11 is an end view of a circular track actuator mechanism in position and surrounding a disclosed IM nail.
Figure 12:
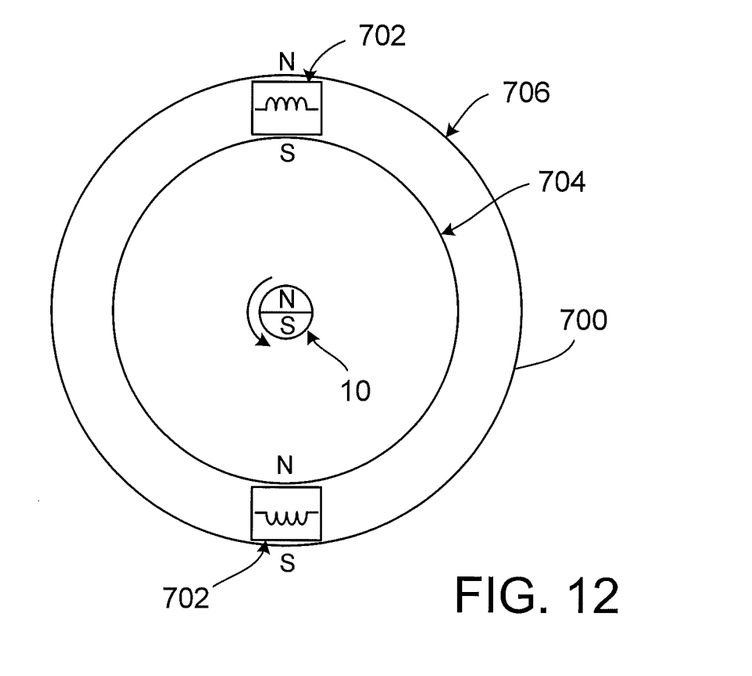
FIG. 12 is an end view of another circular track actuator mechanism in position and surrounding a disclosed IM nail.

FIGS. 11 and 12 illustrate a circular track actuator 700 that houses one or more magnets 702 that are driven to run along inner and outer tracks 704, 706 of the actuator 700. In FIG. 11, two permanent magnets are shown, though any number of permanent magnets appropriately oriented can be driven to run along the tracks, such that the magnets drive the inner magnet of the nail 10 in axial rotation. In FIG. 12, two electromagnets are pulsed and synced, such that the magnets drive the inner magnet of the nail 10 in axial rotation. One or more than one electromagnet can be used to accomplish this. When multiple magnets 702 are used in the tracks of FIGS. 11 and 12, the magnets are linked together to maintain their relative angular orientation. The magnet(s) can be driven mechanically, for example, using a handle, or by a motor or mechanisms described above.

Figure 13:
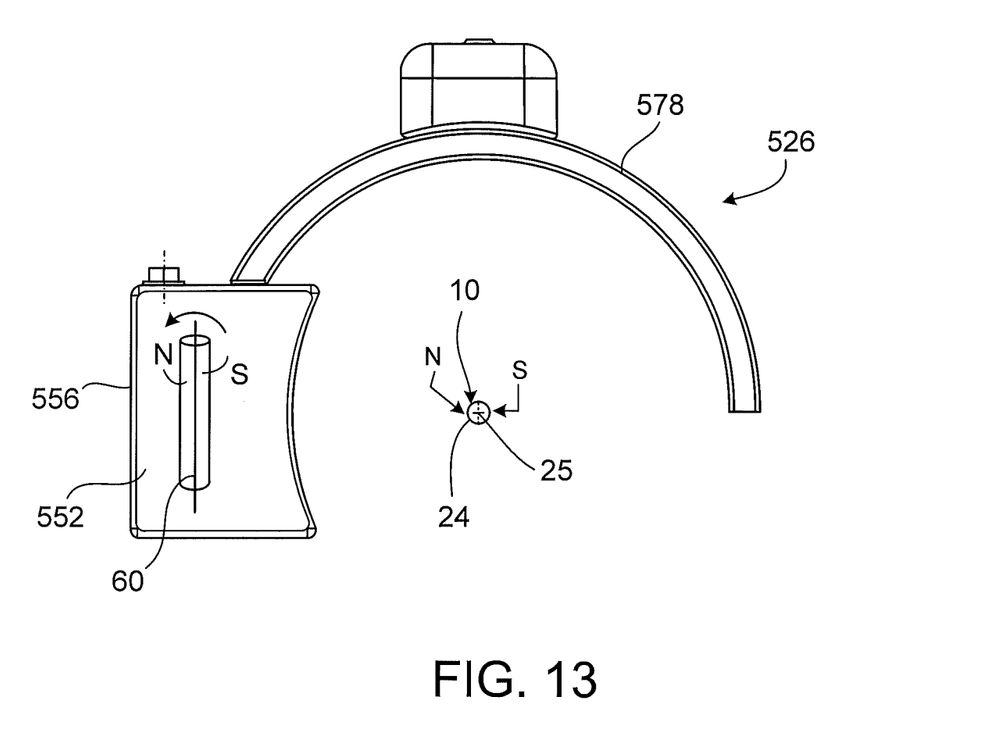
FIG. 13 is an end view of another disclosed single-magnet actuator mechanism in position and surrounding a disclosed IM nail.

Turning to FIG. 13, another disclosed actuator 526 is shown with a single outer magnet 552. The arcuate housing 578 surrounds the IM nail 10. The inner magnet is shown at 24 and the north-south coordinates for the inner magnet 24 as well as the single magnet 552 are also illustrated. The outer magnet 552 is accommodated within a housing 556 and is rotatable about the axis 60. In this embodiment, rather than being parallel to IM nail axis 25, axis 60 is rotated tangentially relative to arcuate housing 578 to form an angle that is between greater than zero and up to +/−90 degrees, with a 90 degree angle being illustrated. The non-parallelism of the rotation axes, for example, the illustrated perpendicular arrangement, allows for a greater actuation distance (i.e., the shortest distance between the magnets), for example, about 50% greater, as compared to the arrangement in which the axes are parallel. For magnet 24 and 552 of the same size, a 90 degree angle provides the greatest actuation distance. The greater actuation distance accommodates patient's with larger legs.

The actuator 526 can include more than one outer magnet, such as illustrated in FIGS. 8-10, but with the additional outer magnets oriented non-parallel to the IM nail axis. In addition or alternatively, additional outer magnets can be oriented parallel to the IM nail axis.

Industrial Applicability

The disclosed IM nail 10 utilizes a telescoping structure in the form of a proximal outer body 12 coupled to a distal body 18 by a threaded rod 28 and threaded block 46. Both distraction and compaction of the proximal and distal bodies 18 with respect to each other is possible. Typically, a patient's bone is severed via an osteotomy for purposes of lengthening the bone over time. The IM nail 10 may employ neodymium magnets for the inner and outer magnets 24, 52, 54, 152, 352, 452 to actuate rotation of the threaded rod 28. Rotation of the threaded rod 28, in turn, results in axial movement the proximal outer body 12 with respect to the distal body 18. When both the proximal outer body 12 and distal body 18 are affixed to portions of the segmented bone, the segmented portions of the bone may be distracted or contracted as necessary by rotation of the threaded rod 28/inner magnet 24. In the embodiments shown, the threaded rod 28 is under tension during axial loading conditions such as standing/ambulating or distraction and contraction of the IM nail 10.

The external actuating mechanisms 26, 26a, 126, 226, 326, 426 are designed to provide sufficient torque to rotate the inner magnet 24 despite the distance between the inner magnet 24 and outer magnets 52, 54, 152, 352, 452. Rotation of the inner magnet 24 must also overcome any compressive load imparted by associated soft tissue of the patient. Accordingly, the position of the outer magnets 52, 54, 152, 352, 452 may be used maximize torque to the inner magnet 24 and threaded rod 28 assembly. A preferred orientation is illustrated in FIG. 8, where the axes 25, 60, 262 of the inner and outer magnets 24, 52, 54 form an angle of about 120°. Accordingly, radially magnetized inner and outer magnets 24, 52, 54, 152, 352, 452, a small diameter threaded rod 28 and the proximal outer body 12 and distal body 18 of the telescoping IM nail 10 can be used to illicit both distraction and contraction of several portions of a diaphyseal bone.

In one embodiment, the threaded rod 28 is affixed to the inner magnet 24, eliminating any degrees of freedom other than axial rotation of the inner magnet 24 and axial rotation of the threaded rod 28. The bearings 32, 36 enable the inner magnet 24 to rotate freely within the proximal outer body 12. The distal body 18 is dimensioned so that the proximal outer body 12 is free to move either axial direction with respect to the distal body 18. The telescoping ability of the IM nail 10 allows the IM nail 10, when affixed to bone via the proximal outer body 12 and distal body 18, to both distract and contract adjacent pieces of bone. The proximal end 20 of the distal body 18 includes a through hole through which the threaded rod 28 can freely pass. The threaded rod 28 is then threadably connected to the threaded block 46 via matching threads. The distal body 18 includes an elongated slot 30 or other structure to permit the threaded block 46 to slide freely in either axial direction. Various means can be used to affix or couple the threaded block 46 to the proximal outer body 12. The distal block 42 is preferably coupled or affixed to the distal body 18 and the threaded rod 28 and end cap 44 can rotate freely without an alteration of the position of the distal end 40 of the threaded rod 28 with respect to the distal body 18.

The larger proximal outer body 12 moves axially with the threaded block 46 during distraction, contraction and loading. As a result, the threaded rod 28 is maintained in a constant tension. Because the threaded rod 28 is not compressed, the strength of the IM nail 10 structure is increased and binding between the threads of the threaded rod 28 and threaded block 46 are minimized. More specifically, during distraction, the points of contact between the threaded rod 28/inner magnet 24 are at the threaded rod 28, threaded block 46 interface and at the junction between the inner magnet 24 and the proximal end 20 of the distal body 18 as illustrated in FIG. 2. During contraction, the points of contact between the threaded rod 28/inner magnet 24 are disposed at the threaded rod 28/threaded block 46 interface and at the junction between the inner magnet 24 (or magnet carrier) and the proximal end of the distal body 18 as illustrated in FIG. 1. As a result, the loading forces in either axial direction during contraction or distraction are located at essentially the same interfaces.

While neodymium magnets are suggested, other magnets may be employed as will be apparent to those skilled in the art. The first and second outer magnets 52, 54 are preferably disposed at an angle θ ranging from about 120 to about 180° with respect to each other and the arcuate linkages 74, 274, 374, 474, 574 and arcuate housings 78, 178, 278, 378, 478 are preferably dimensioned to accommodate a patient's limb in which an IM nail 10 has been inserted. To accomplish these objectives, each outer magnet 52, 54, 152, 352, 452 may be mounted within its own housing 56, 58, 356, 456 and a singular actuating mechanism 68, 70, 72, 74, 274, 76, 372, 474, 478 either interior or exterior to the housings 56, 58 may be employed to spin both magnets in the same direction as illustrated in FIGS. 3 and 8. Upon actuation, the spinning of the first and second outer magnets 52, 54, or single outer magnet 152 will provide additive torque to the inner magnet 24 housed within the IM nail 10.

As will be apparent to those skilled in the art, different types of permanent magnets, electro magnets, different magnet shapes and different mounting types or locations of the magnets 24, 52, 54, 152 may be employed. The structure of the housings 56, 58, 78, 178, 278 may also vary in terms of shape, relative dimensions and construction. The linkage between the magnets 52, 54 (see 72, 74, 76 in FIGS. 3 and 8) can be accomplished by a variety of means such as a flexible drive mechanism, gearing combinations, belt drives, worm gears, hydraulic drives, pneumatic drives, hydrostatic drives, chain drives, bar linkage drives, etc. The mechanical link between the magnets 52, 54, 152 and the housings 56, 58, 156 may also vary using flexible drive mechanisms, gearing combinations, belt drives, worm gears, hydraulic drives, pneumatic drives, hydrostatic drives, chain drives, bar linkage drives, etc.

Further, the magnets 52, 54, 24, 152 may be oriented in configurations or directions other than axially such as 360° circumferential rotation, e.g. spun around the axis of the limb rather than the axis of the inner magnet 24). The magnets 52, 54, 152 could also be driven in a linear direction in either a continual (constant force) or pulsing action. The location of the actuation mechanism 68, 70 could be disposed in either housing 56, 58, within the arcuate housing 78, 178, 278, on the user interface 80 or outside of the housings 56, 58, 78, 178, 278 altogether. The actuator button 68 may be provided in the form of a helical push button, turn handle, linear gearing, worm gearing, spur gears, helical gears, rack and pinion gears, pawls, hydraulic actuation, pneumatic actuation, hydrostatic actuation, magnetic actuation, brush and brushless electrical motors, including stepper motors. The lengthening monitor or user interface 80 may be solid state or an electro-mechanical device. The interface 80 may also be a wireless device that would not appear on the housing. The information to be displayed would be shown on a monitor in the operating room. Hence, the interface 80 and display panel 82 are truly optional, given the wireless technology that is currently available. The interface 80 may measure pull changes of the inner magnet 24 or linear movement of the inner magnet 24. The display 82 of the interface 80 may be analog or digital. The specific information displayed on the display 82 may vary depending upon need and may be programmable by the surgeon or physician. The interface 80 may also employ alarms or alerts to warn the physician or user of distraction/contraction that deviates from the original prescription.

While only certain embodiments have been set forth, alternatives and modifications will be apparent from the above description to those skilled in the art. These and other alternatives are considered equivalents and within the spirit and scope of this disclosure and the appended claims.

The invention claimed is:
1. A length adjustable intramedullary nail system, comprising:
    an intramedullary nail, comprising:
        a proximal outer body;
        a distal body having a portion received by the proximal outer body;

a threaded shaft coupled to the distal body to rotate relative thereto without relative axial movement;

an inner magnet received by the proximal outer body and coupled to the threaded shaft for rotation therewith; and a threaded block coupled to the proximal outer body and having internal threads, the threaded shaft passing through the threaded block and threadedly engaging with the internal threads such that rotation of the inner magnet and the threaded shaft relative to the threaded block causes relative axial movement between a) the inner magnet, the threaded shaft and the distal body and b) the proximal outer body.

2. The system of claim 1 wherein the threaded shaft is connected to the distal body at a fixed position such that the threaded shaft and the distal body are axially fixed relative to each other.

3. The system of claim 1 further comprising an actuator including at least one outer magnet.

4. The system of claim 3 further comprising a housing rotatably accommodating the at least one outer magnet and accommodating a drive mechanism configured to rotate the outer magnet about an axis that is parallel to an axis of the inner magnet, such that rotation of the outer magnet imparts rotation to the inner magnet.

5. The system of claim 3 wherein the at least one outer magnet comprises two outer magnets.

6. The system of claim 5 further comprising first and second housings each rotatably accommodating one of the outer magnets and each accommodating a drive mechanism configured to rotate the one of the outer magnets about an axis that is parallel to an axis of the inner magnet, such that rotation of the outer magnets imparts rotation to the inner magnet.

7. The system of claim 6 wherein the housings are coupled together to maintain the first and second outer magnets in a spaced-apart angular relationship to permit the intramedullary nail to be positioned between the first and second outer magnets.

8. The system of claim 7 further comprising a linkage coupling the first and second outer magnets and configured to impart rotation to the first and second outer magnets in the same direction to impart rotation to the inner magnet and threaded shaft.

9. The system of claim 3 further comprising a circular track accommodating the at least one outer magnet.

10. The system of claim 3 wherein the actuator comprises a user interface that displays the magnitude of axial distraction or axial compaction of the intramedullary nail.

11. The system of claim 3 wherein the at least one outer magnet comprises a first outer magnet, the system further comprising a housing rotatably accommodating the first outer magnet and accommodating a drive mechanism configured to rotate the first outer magnet about an axis that is non-parallel to an axis of the inner magnet, such that rotation of the first outer magnet imparts rotation to the inner magnet.

12. The system of claim 11 wherein the rotation axis of the first outer magnet is perpendicular to the axis of the inner magnet.

13. The system of claim 11 wherein the rotation axis of the first outer magnet forms an angle with the axis of the inner magnet that is between greater than zero and up to 90 degrees.

14. The system of claim 11 wherein the actuator comprises a user interface that displays the magnitude of axial distraction or axial compaction of the intramedullary nail.

15. The system of claim 11 wherein the at least one outer magnet further comprises one or more additional outer magnets.

16. The system of claim 15 wherein at least one of the one or more additional outer magnets is configured to rotate about an axis that is non-parallel to the axis of the inner magnet.

17. The system of claim 15 wherein at least one of the one or more additional outer magnets is configured to rotate about an axis that is parallel to the axis of the inner magnet.

18. The system of claim 1 wherein the distal body of the intramedullary nail includes at least one transverse hole for receiving a fixation element to couple the distal body to a patient's bone.

19. The system of claim 1 wherein the threaded block is fixedly attached to a distal end of the proximal outer body.

20. The system of claim 1 wherein a proximal end of the threaded shaft is coupled to a distal end of the inner magnet.

21. The system of claim 20 wherein the proximal end of the threaded shaft abuts the distal end of the inner magnet.

22. The system of claim 1 wherein at least a portion of the threaded shaft is received within the distal body.

23. The system of claim 1 wherein a total area of threaded engagement between the threaded block and the threaded shaft remains substantially the same throughout a range of the relative axial movement between a) the inner magnet, the threaded shaft and the distal body and b) the proximal outer body.

* * * * *